(12) United States Patent
Wang et al.

(10) Patent No.: US 11,655,489 B2
(45) Date of Patent: May 23, 2023

(54) METHOD FOR IMPROVING N-3 POLYUNSATURATED FATTY ACIDS ENRICHMENT EFFICIENCY IN GLYCERIDE

(71) Applicant: Jiangnan University, Wuxi (CN)

(72) Inventors: Xiaosan Wang, Wuxi (CN); Ye Chen, Wuxi (CN); Cong Jiang, Wuxi (CN); Zhuangzhuang Yang, Wuxi (CN); Yifan Wang, Wuxi (CN); Wenhua Jin, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/411,076

(22) Filed: Aug. 25, 2021

(65) Prior Publication Data

US 2022/0119852 A1    Apr. 21, 2022

(51) Int. Cl.
    *C12P 7/6472*    (2022.01)
(52) U.S. Cl.
    CPC ................................. *C12P 7/6472* (2013.01)
(58) Field of Classification Search
    CPC ....................... C12Y 301/01003; C12P 7/6472
    See application file for complete search history.

(56) References Cited

U.S. PATENT DOCUMENTS

| | | | | |
|---|---|---|---|---|
| 9,034,612 B2* | 5/2015 | Lam | ....................... | C12P 7/6418 435/195 |
| 2014/0193866 A1* | 7/2014 | Lam | ....................... | C12P 7/6481 435/134 |
| 2015/0344918 A1* | 12/2015 | Lam | ....................... | C12P 7/6481 435/134 |
| 2016/0168504 A1* | 6/2016 | Lee | ....................... | C10M 111/04 508/505 |

\* cited by examiner

*Primary Examiner* — Tekchand Saidha
(74) *Attorney, Agent, or Firm* — Idea Intellectual Limited; Margaret A. Burke; Sam T. Yip

(57) ABSTRACT

This invention discloses a method for improving n-3 polyunsaturated fatty acid enrichment efficiency in glyceride, belonging to the field of deep processing of oil. The method of this invention includes providing oil, lipase and metal ionic liquid into a reactor. After a reaction time, a mixture is obtained and free fatty acid is removed from the mixture, and the product is the n-3 polyunsaturated fatty acid-rich glyceride. Compared with the traditional chemical method, the method of this invention is characterized by mild reaction conditions and producing lower level of by-products. Meanwhile, metal ions selected in the present invention are able to promote the hydrolysis of lipase, solving the problem of long reaction time in the conventional enzymatic method. Rapid hydrolysis is achieved by this method so as to realize enrichment of EPA and DHA in glyceride.

8 Claims, 4 Drawing Sheets

METHOD FOR IMPROVING N-3 POLYUNSATURATED FATTY ACIDS ENRICHMENT EFFICIENCY IN GLYCERIDE

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCES TO RELATED APPLICATIONS

This application claims priority from Chinese patent application number 202011111068.9 filed on Oct. 16, 2020, and the disclosure of which are incorporated herein by reference in their entirety.

FIELD OF THE INVENTION

The present invention relates to a method for improving n-3 polyunsaturated fatty acids enrichment efficiency in glyceride, belonging to the field of deep processing of oil.

BACKGROUND OF THE INVENTION n-3 polyenoic acids (n-3 PUFAs) have biological significance to human body, especially eicosapentaenoic acid (EPA) and docosahexaenoic acid (DHA), which can significantly prevent and treat cardiovascular diseases, assist in post-inflammation recovery, and promote normal development of sensory organs in infants. Therefore, they are widely used in healthcare food and drugs.

There are three types of n-3 PUFAs-containing products available on the market: ethyl ester-type, glyceride-type and free fatty acid-type. The content of n-3 PUFAs in the glyceride-type products is relatively low, which is about 30% that is unable to satisfy people's healthcare and medical needs. The content of n-3 PUFAs in the ethyl ester-type and free fatty acid-type products could reach 90%. However, it is relatively difficult for human to digest and absorb ethyl ester fish oil and the free fatty acid type is poor in stability. Therefore, the condensed glyceride type is the best choice.

Enzymatic method is commonly used in conventional bio-manufacturing. Compared with the traditional chemical method, enrichment of n-3 PUFAs by means of the enzymatic method is green, safe and produces lower level of by-products. However, the reaction time of the existing enzymatic method is generally long, 10-36 h, even longer, so costs are higher. Therefore, it is urgent to find a method for enrichment of n-3 PUFAs which is able to shorten the reaction time of the enzymatic method and meet the green and safe concepts.

SUMMARY OF THE INVENTION

Considering the time-consuming problem existing in the above and/or existing methods for enrichment of n-3 polyunsaturated fatty acid in glyceride in oil, this invention provides a method for improving the n-3 polyunsaturated fatty acid in glyceride enrichment efficiency. By the present method, the result obtained within 2 h is comparable to that obtained by conventional enzymatic method for 6-12 h, or even longer. Therefore, the present method provides important technical merit for industrialization of enrichment of n-3 polyunsaturated fatty acid in glyceride in oil by means of the enzymatic method.

To solve the technical problems mentioned in the previous section, the present invention provides a method for improving n-3 polyunsaturated fatty acid in glyceride enrichment efficiency. The method includes providing oil, lipase, metal ions and aqueous solution into a reactor, obtaining a mixture after a reaction time from the reactor, and removing the free fatty acid from the mixture to obtain n-3 polyunsaturated fatty acid-rich in glyceride.

In one embodiment, the lipase is selected from *Candida cylindracea* lipase, *Rhizopus oryzea* lipase, *Candida antarctica* lipase A of *Candida antarctica* and one or more of *Aspergillus* sp. lipase.

In one embodiment, the metal ions including one or several of calcium ions ($Ca^{2+}$), magnesium ions ($Mg^{2+}$), manganese ions ($Mn^{2+}$) and ferric ions ($Fe^{3+}$).

In one embodiment, the concentration of the metal ions is 5-50 mmol/L.

In one embodiment, the aqueous solution includes one or more of pure water solution, phosphate buffered solution and citrate buffered solution. The concentration of the buffer salt solution is 0.05-0.5 mol/L.

In one embodiment, the reaction in the reactor is carried out at pH 5-8.

In one embodiment, the oil contains n-3 polyunsaturated fatty acid.

In one embodiment, the oil includes fish oil, algal oil and flaxseed oil.

In one embodiment, the mass ratio between the aqueous solution and oil is 0.2-3:1.

In one embodiment, the reaction time is 1-12 h and reaction temperature is 20-50° C.

In a preferred embodiment, the reaction time is 1-4 h; more preferably is 2 h.

In one embodiment, the volume of addition of the lipase is 150-15000 U/g oil.

In one embodiment, the removing of the free fatty acids from the mixture is by alkali refining deacidification or molecular distillation. Preferably, alkali refining deacidification is used.

The followings are some beneficial effects of the present invention:

(1) This invention provides a method for improving n-3 polyunsaturated fatty acid in glyceride enrichment efficiency. In catalytic hydrolysis of lipase, fish oil and algae oil are directly used as raw material and no other organic solvents are added in the reaction process. Raw materials for reaction include fish oil and buffer solution, the catalyst is lipase. Compared with the traditional chemical method, the reaction conditions used in the present invention are mild; by-products therefrom are fewer; and the process is more environment-friendly. Compared with enzymatic transesterification and esterification, the present invention is safer and lower in cost. Compared with the existing enzymatic hydrolysis, the present invention significantly shortens the reaction time, thereby lowering the cost.

(2) Metal ions used in the present invention are able to promote hydrolysis of lipase, thereby significantly shortening the reaction time, that is, only 2 h is required for the desired enrichment effect. Therefore, the present invention is of high industrial production significance. In addition, the lipase used has n-3 PUFAs with strong hydrolysis "discrimination". Based on this feature, saturated and monounsaturated fatty acids could be hydrolyzed rapidly to achieve enrichment of EPA and DHA in glyceride.

Figure 1A:
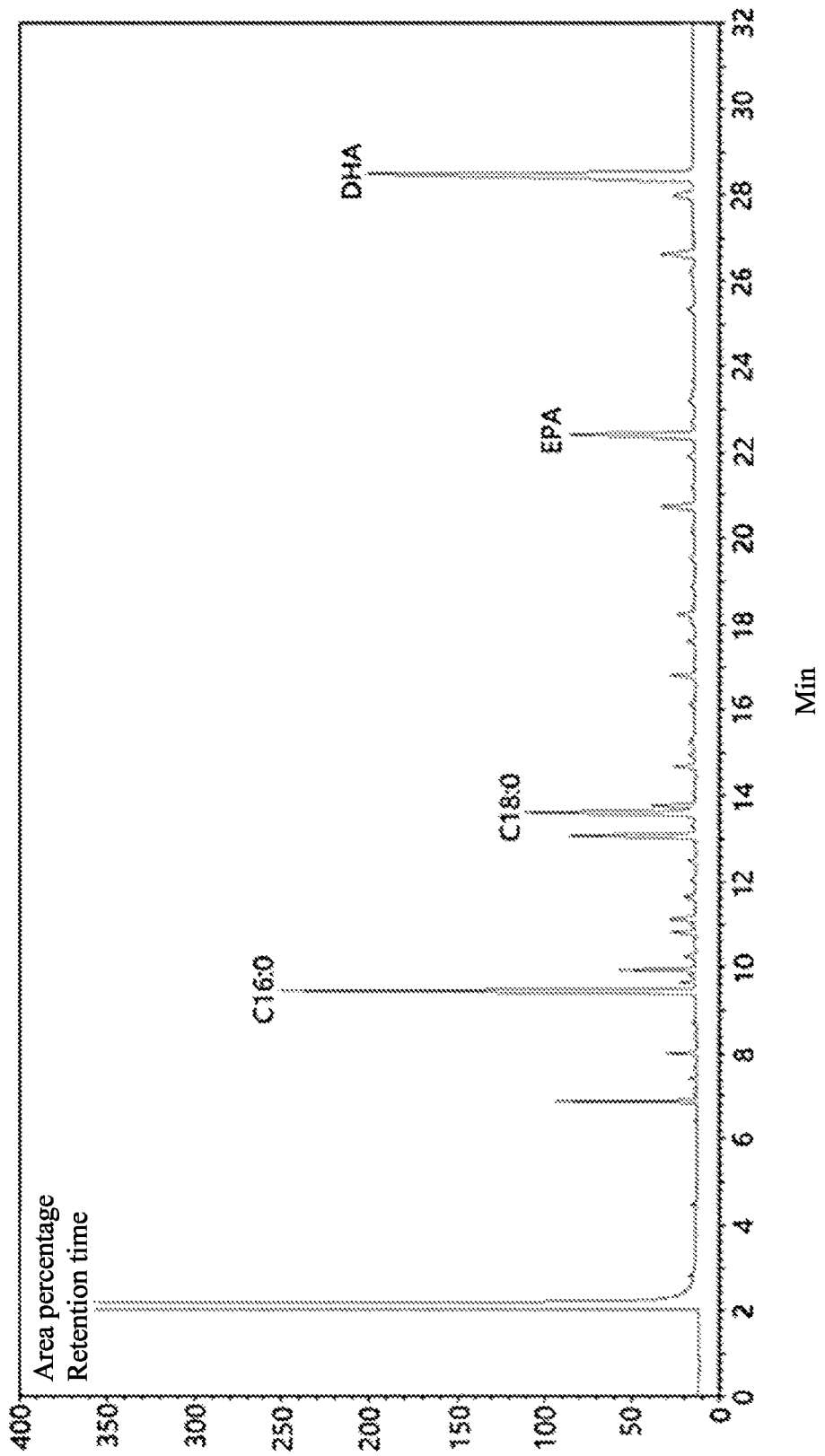
FIG. 1 is a gas chromatogram showing fatty acid composition of glyceride before and after fish oil reaction in Embodiment 1 of this invention, in which "a" represents before reaction and "b" represents after reaction.

DETAILED DESCRIPTION (1) Method for Measurement of the Content of n-3 PUFAs 50 mg of sample was put into a 10-ml graduated tube. 2 ml of 0.5 mol/l potassium hydroxide-methanol solution was then added into the sample to saponify at 65° C. for 30 mins, cooled down, followed by adding 2 ml of boron trifluoride-methanol solution with 25% volume fraction, and subjected to water bath at 70° C. for 5 mins. 2 mL of n-hexane was added and shaken for 3-4 mins to extract fatty acid methyl ester. 4 mL of saturated NaCl solution was added, and the upper portion of the solution was collected and added with anhydrous sodium sulfate for sonication (followed by centrifugation at 10000 rpm for 5 mins). A syringe was used to suction the supernatant through a membrane and the filtered solution was subjected to gas chromatography analysis. The followings are operation parameters of gas chromatography: 7890 gas chromatograph system was used, with flame ionization detector (FID); dimension of gas chromatographic column was 60 m×0.32 mm×2.5 μm; nitrogen flow rate was set at 1.0 mL/min; and the temperature of the sample injector and detector was set at 250° C. The initial column temperature was maintained at 80° C. for 0.5 min, and then increased to 165° C. at the rate of 40° C./min. The column temperature is increased to 230° C. at the rate of 4° C./min and maintained for 4 mins. The peak area normalization was used to calculate the content of n-3 PUFAs.

(2) Method for Analysis of Hydrolysates 20 mg of the hydrolysates was added with 1 mL of mobile phase (n-hexane:Isopropyl alcohol:Methanoic acid=15:1: 0.003) for dissolution, followed by membrane filtering and liquid chromatography. Operation parameters of the liquid chromatography are as follows:

HPLC, Sepax HP silica gel column (pore diameter of 5 μm, 4.6 mm×250 mm) differential refractive index detector; elute at a rate of 1.0 mL/min with hexane, isopropanol and formic acid (15:1:0.003, v/v/v). Peak area normalization was used to calculate the content of free fatty acid after hydrolysis.

In order to better illustrate the aforesaid objectives, features and advantages of this invention, specific embodiments of this invention are described hereinafter accompanied with examples.

The description below contains many specific details for full understanding of this invention, but this invention may be embodied in other modes different from those described herein. Those skilled in the art can make similar promotion without violating the connotation of this invention. Therefore, this invention is not limited by the specific embodiments disclosed below.

Then, "one embodiment" or "embodiments" referred here refer to those containing specific features, structure or characteristics of at least one implementation mode of this invention. "In one embodiment" appearing in different places of this specification does not refer to the same embodiment, nor a separate embodiment or embodiment selectively exclusive with other embodiments.

The lipases coming from *Candida cylindracea*, *Rhizopus oryzea*, *Candida antarctica* and *Aspergillus* sp. are all commercially available.

Oils used in this invention are all available on the market, among which, fish oil (tuna oil) n-3 PUFAs content=34.3%; Algae oil n-3 PUFAs content=46.0%. Other reagents are all available on the market unless there are special instructions.

Calculation formula of hydrolysis rate:

$$\text{Hydrolysis rate \%} = \frac{\text{Specific mass of glyceride before hydrolysis} - \text{specific mass of glyceride in mixed products after hydrolysis}}{\text{Specific mass of glyceride before hydrolysis}} \times 100$$

Where, the said specific mass of glyceride is obtained through the following method or calculation formula:

Mass fraction % of glyceride=mass fraction % of triglyceride+mass fraction % of diglyceride+mass fraction % of monoglyceride obtained through HPLC method.

Embodiment 1

Figure 1B:
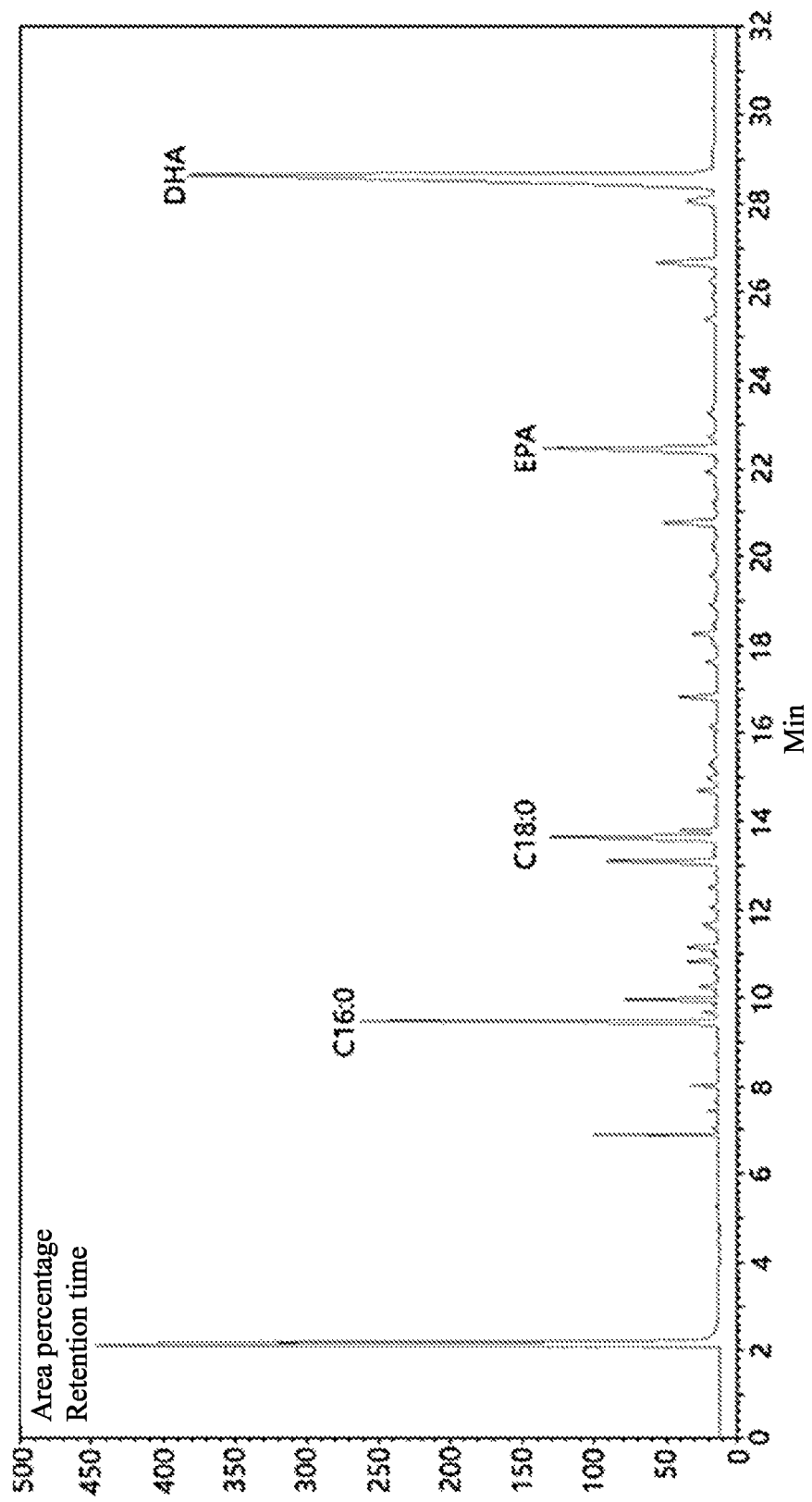
Figure 2A:
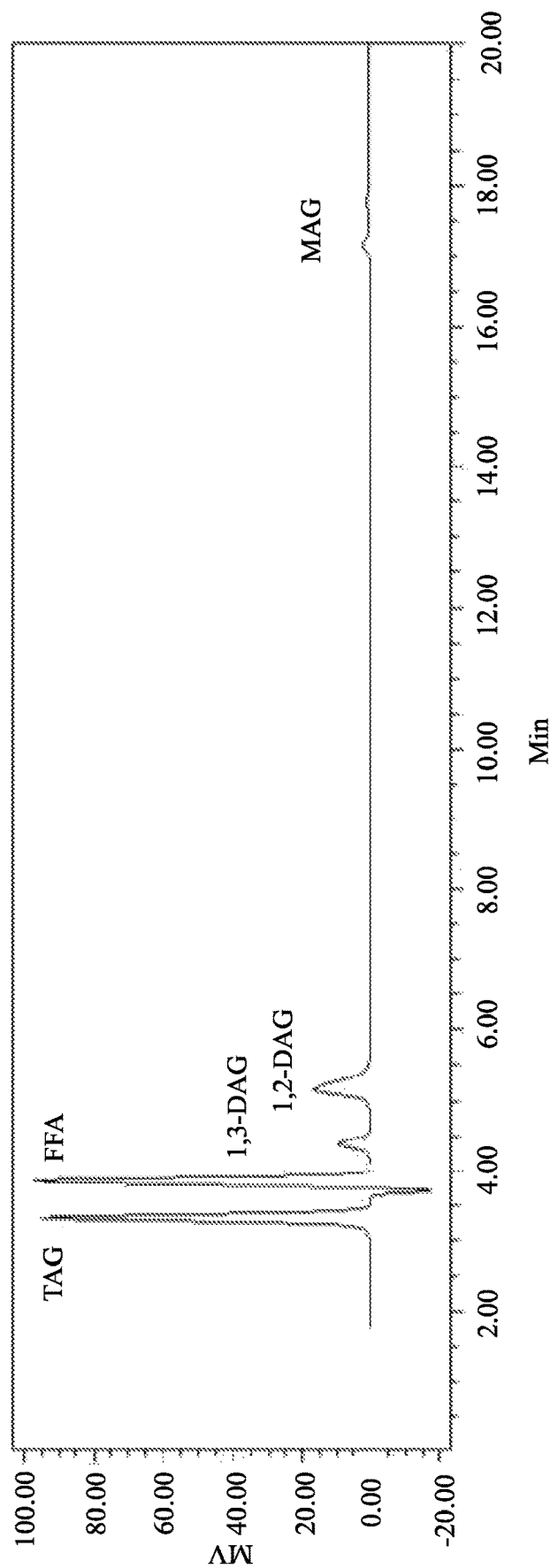
FIG. 2 is the chromatogram of liquid (differential refractive index detector) chromatography of oil phase product composition after hydrolysis of fish oil in this invention, in which, "a" is the chromatogram of the hydrolysate composition analysis in Embodiment 1 and "b" is the chromatogram of the hydrolysate composition analysis in Comparative Embodiment 1.

3.0 g of fish oil (fatty acid composition of fish oil sample is shown in FIG. 1a, in which n-3 PUFAs content=34.3%), 3 g of calcium ion (20 mmol/L)-aqueous solution and 960U (2.4 mg) of *Candida cylindracea* lipase were accurately weighed, then they were put into a reactor with a magnetic stir bar and sealed. The reactor was placed on a magnetic stirrer. The reactor was connected to a water circulation system and the water temperature was kept at 37° C. for 2 h. The hydrolysis rate is 41.2% (as shown in FIG. 2a). When the reaction completed, KOH-ethanol aqueous solution was used to remove the free fatty acid after hydrolysis. After washing with water for three times, the upper, clear oil phase was collected and the solvent therein was evaporated to obtain the fish oil-rich glyceride in n-3 PUFAs. In the fatty acid composition of glyceride products, the content of n-3 PUFAs is increased from 34.3% in the crude oil to 60.3% after hydrolysis (as shown in FIG. 1b).

Embodiment 2

Similar to Embodiment 1, except the type of metal ion in the reaction system of this embodiment was different, which was magnesium ion (20 mmol/L), the rest of the procedures and conditions were identical. The hydrolysis rate and the content of n-3 PUFAs in glyceride obtained in this embodiment are shown in Table 1.

Embodiment 3

Similar to Embodiment 1, except the type of metal ion in the reaction system of this embodiment was different, which was manganese ion (20 mmol/L), the rest of the procedures and conditions were identical. The hydrolysis rate and the content of n-3 PUFAs in glyceride obtained are shown in Table 1.

Embodiment 4

Similar to Embodiment 1, except the type of metal ion in the reaction system of this embodiment was different, which was ferric ion (20 mmol/L), the rest of the procedures and conditions were identical. The hydrolysis rate and the content of n-3 PUFAs in glyceride obtained are shown in Table 1.

Embodiment 5

Similar to Embodiment 1, except the types of metal ion and aqueous solution in the reaction system of this embodiment were different, which were calcium ion (20 mmol/L) and phosphate buffered solution (0.1 mol/L, pH 7), respectively, the rest of the procedures and conditions were identical. The hydrolysis rate and the content of n-3 PUFAs in glyceride obtained are shown in Table 1.

Embodiment 6

Similar to Embodiment 1, except the types of metal ion and aqueous solution in the reaction system of this embodiment were different, which were calcium ion (20 mmol/L) and citrate buffered solution (0.1 mol/L, pH 7), respectively, the rest of the procedures and conditions were identical. The hydrolysis rate and the content of n-3 PUFAs in glyceride obtained are shown in Table 1.

Embodiment 7

Similar to Embodiment 1, except the types of metal ion and aqueous solution in the reaction system of this embodiment were different, which were magnesium ion (20 mmol/L) and phosphate buffered solution (0.1 mol/L, pH 7), respectively, the rest of procedures and conditions were identical. The hydrolysis rate and the content of n-3 PUFAs in glyceride obtained are shown in Table 1.

Embodiment 8

Similar to Embodiment 1, except the concentration of calcium ion in the reaction system of this embodiment was different, which was 10 mmol/L, the rest of the procedures and conditions were identical. The hydrolysis rate and the content of n-3 PUFAs in glyceride obtained are shown in Table 1.

Embodiment 9

Similar to Embodiment 1, except the concentration of calcium ion in the reaction system of this embodiment was different, which as 40 mmol/L, the rest of the procedures and conditions were identical. The hydrolysis rate and the content of n-3 PUFAs in glyceride obtained are shown in Table 1.

Embodiment 10

Similar to Embodiment 1, except the type and the volume of lipase added into the reaction system of this embodiment were different, which were AY "Amano" 30SD and 960U, respectively, the rest of procedures and conditions were identical. The hydrolysis rate and the content of n-3 PUFAs in glyceride obtained are shown in Table 1.

Embodiment 11

Similar to Embodiment 10, except the type of metal ion in the reaction system of this embodiment was different, which was magnesium ion (20 mmol/L), the rest of the procedures and conditions were identical. The hydrolysis rate and the content of n-3 PUFAs in glyceride obtained are shown in Table 1.

Embodiment 12

Similar to Embodiment 10, except the type of metal ion in the reaction system of this embodiment was different, which was manganese ion (20 mmol/L), the rest of the procedures and conditions were identical. The hydrolysis rate and the content of n-3 PUFAs in glyceride obtained are shown in Table 1.

Embodiment 13

Similar to Embodiment 10, except the type of metal ion in the reaction system of this embodiment was different, which was ferric ion (20 mmol/L), the rest of the procedures and conditions were identical. The hydrolysis rate and the content of n-3 PUFAs in glyceride obtained are shown in Table 1.

Embodiment 14

Similar to Embodiment 1, except the type and the volume of lipase added into the reaction system of this embodiment were different, which was 960U of *Rhizopus oryzea* lipase, the rest of the procedures and conditions were identical. The hydrolysis rate and the content of n-3 PUFAs in glyceride obtained are shown in Table 1.

Embodiment 15

Similar to Embodiment 14, except the type of metal ion in the reaction system of this embodiment was different, which was magnesium ion (20 mmol/L), the rest of the procedures and operations were identical. The hydrolysis rate and the content of n-3 PUFAs in glyceride obtained are shown in Table 1.

Embodiment 16

Similar to Embodiment 14, except the type of metal ion in the reaction system of this embodiment was different, which was manganese ion (20 mmol/L), the rest of the procedures and conditions were identical. The hydrolysis rate and the content of n-3 PUFAs in glyceride obtained are shown in Table 1.

Embodiment 17

Similar to Embodiment 14, except the type of metal ion in the reaction system of this embodiment was different, which was ferric ion (20 mmol/L), the rest of the procedures and conditions were identical. The hydrolysis rate and the content of n-3 PUFAs in glyceride obtained are shown in Table 1.

Embodiment 18

Similar to Embodiment 1, except the type and volume of lipase added into the reaction system of this embodiment were different, which were *Candida antarctica* lipase A and 960U, respectively, the rest of the procedures and conditions were identical. The hydrolysis rate and the content of n-3 PUFAs in glyceride obtained are shown in Table 1.

Embodiment 19

Similar to Embodiment 18, except the type of metal ion in the reaction system of this embodiment was different, which was magnesium ion (20 mmol/L), the rest of the procedures and conditions were identical. The hydrolysis rate and the content of n-3 PUFAs in glyceride obtained are shown in Table 1.

Embodiment 20

Similar to Embodiment 18, except the type of metal ion in the reaction system of this embodiment was different, which was manganese ion (20 mmol/L), the rest of the procedures and conditions were identical. The hydrolysis rate and the content of n-3 PUFAs in glyceride obtained are shown in Table 1.

Embodiment 21

Similar to Embodiment 18, except the type of metal ion in the reaction system of this embodiment was different, which was ferric ion (20 mmol/L), the rest of the procedures and conditions were identical. The hydrolysis rate and the content of n-3 PUFAs in glyceride obtained are shown in Table 1.

Embodiment 22

Similar to Embodiment 1, except the type and the volume of lipase added into the reaction system of this embodiment were different, which were 960U of *Aspergillus* sp. lipase, the rest of the procedures and conditions were identical. The hydrolysis rate and the content of n-3 PUFAs in glyceride obtained are shown in Table 1.

Embodiment 23

Similar to Embodiment 22, except the type of metal ion in the reaction system of this embodiment was different, which was magnesium ion (20 mmol/L), the rest of the procedures and conditions were identical. The hydrolysis rate and the content of n-3 PUFAs in glyceride obtained are shown in Table 1.

Embodiment 24

Similar to Embodiment 22, except the type of metal ion in the reaction system of this embodiment was different, which was manganese ion (20 mmol/L), the rest of the procedures and conditions were identical. The hydrolysis rate and the content of n-3 PUFAs in glyceride obtained are shown in Table 1.

Embodiment 25

Similar to Embodiment 22, except the type of metal ion in the reaction system of this embodiment was different, which was ferric ion (20 mmol/L), the rest of the procedures and conditions were identical. The hydrolysis rate and the content of n-3 PUFAs in glyceride obtained are shown in Table 1.

Embodiment 26

Similar to Embodiment 1, except the type of oil in the reaction system of this embodiment was different, which was algal oil, the rest of the procedures and conditions were identical. The hydrolysis rate and the content of n-3 PUFAs in glyceride obtained are shown in Table 1.

Embodiment 27

Similar to Embodiment 26, except the type of metal ion in the reaction system of this embodiment was different, which was magnesium ion (20 mmol/L), the rest of the procedures and conditions were identical. The hydrolysis rate and the content of n-3 PUFAs in glyceride obtained are shown in Table 1.

Embodiment 28

Similar to Embodiment 26, except the types of metal ion and aqueous solution in the reaction system were different, which were calcium ion (20 mmol/L) and phosphate buffered solution (0.1 mol/L, pH 7), respectively, the rest of the procedures and conditions were identical. The hydrolysis rate and the content of n-3 PUFAs in glyceride obtained are shown in Table 1.

Embodiment 29

Similar to Embodiment 26, except the type and volume of lipase added into the reaction system of this embodiment were different, which were 960U of *Candida cylindracea* lipase, the rest of the procedures and conditions were identical. The hydrolysis rate and the content of n-3 PUFAs in glyceride obtained are shown in Table 1.

Embodiment 30

Similar to Embodiment 26, except the type and volume of lipase added into the reaction system of this embodiment were different, which were 960U of *Rhizopus oryzea* lipase, the rest of the procedures and conditions were identical. The hydrolysis rate and the content of n-3 PUFAs in glyceride obtained are shown in Table 1.

Embodiment 31

Similar to Embodiment 26, except the type and volume of lipase added into the reaction system of this embodiment were different, which were *Candida antarctica* lipase A and 960U, respectively, the rest of the procedures and conditions were identical. The hydrolysis rate and the content of n-3 PUFAs in glyceride obtained are shown in Table 1.

Embodiment 32

Similar to Embodiment 26, except the type and volume of lipase added into the reaction system of this embodiment were different, which 960U of *Aspergillus* sp. lipase, the rest of the procedures and conditions were identical. The hydrolysis rate and the content of n-3 PUFAs in glyceride obtained are shown in Table 1.

Embodiment 33

Similar to Embodiment 1, except the reaction time in the reaction system of this embodiment was different, which was 1 h, the rest of the procedures and conditions were identical. The hydrolysis rate and the content of n-3 PUFAs in glyceride obtained are shown in Table 1.

Embodiment 34

Similar to Embodiment 1, except the reaction time in the reaction system of this embodiment was different, which was 4 h, the rest of the procedures and conditions were identical. The hydrolysis rate and the content of n-3 PUFAs in glyceride obtained are shown in Table 1.

Embodiment 35

Similar to Embodiment 1, except the types of metal ion and aqueous solution in the reaction system were different, which were calcium ion (20 mmol/L) and phosphate buffered solution (0.1 mol/L, pH 5), respectively, the rest of the procedures and conditions were identical. The hydrolysis rate and the content of n-3 PUFAs in glyceride obtained are shown in Table 1.

Embodiment 36

Similar to Embodiment 1, except the types of metal ion and aqueous solution in the reaction system were different, which were calcium ion (20 mmol/L) and phosphate buffered solution (0.1 mol/L, pH 8), respectively, the rest of the procedures and conditions were identical. The hydrolysis rate and the content of n-3 PUFAs in glyceride obtained are shown in Table 1.

Embodiment 37

Similar to Embodiment 1, except the amount of calcium ion (20 mmol/L) added into the aqueous solution of the reaction system of this embodiment was different, which was 0.9 g, the rest of the procedures and conditions were identical. The hydrolysis rate and the content of n-3 PUFAs in glyceride obtained are shown in Table 1.

Embodiment 38

Similar to Embodiment 1, except the amount of calcium ion (20 mmol/L) added into the aqueous solution of the reaction system of this embodiment was different, which was 6 g, the rest of the procedures and conditions were identical. The hydrolysis rate and the content of n-3 PUFAs in glyceride obtained are shown in Table 1.

Embodiment 39

Similar to Embodiment 1, except the volume of lipase added into the reaction system of this embodiment was different, which was 240U (0.02%), the rest of the procedures and conditions were identical. The hydrolysis rate and the content of n-3 PUFAs in glyceride obtained are shown in Table 1.

Embodiment 40

Similar to Embodiment 1, except the volume of lipase added into the reaction system of this embodiment was different, which was 9600U (0.8%), the rest of the procedures and conditions were identical. The hydrolysis rate and the content of n-3 PUFAs in glyceride obtained are shown in Table 1.

Embodiment 41

Similar to Embodiment 1, except the reaction temperature in the reaction system of this embodiment was different, which was 20° C., the rest of the procedures and conditions were identical. The hydrolysis rate and the content of n-3 PUFAs in glyceride obtained are shown in Table 1.

Embodiment 42

Similar to Embodiment 1, except the reaction temperature in the reaction system of this embodiment was different, which was 50° C., the rest of the procedures and conditions were identical. The hydrolysis rate and the content of n-3 PUFAs in glyceride obtained are shown in Table 1.

Comparative Embodiment 1

Figure 2B:
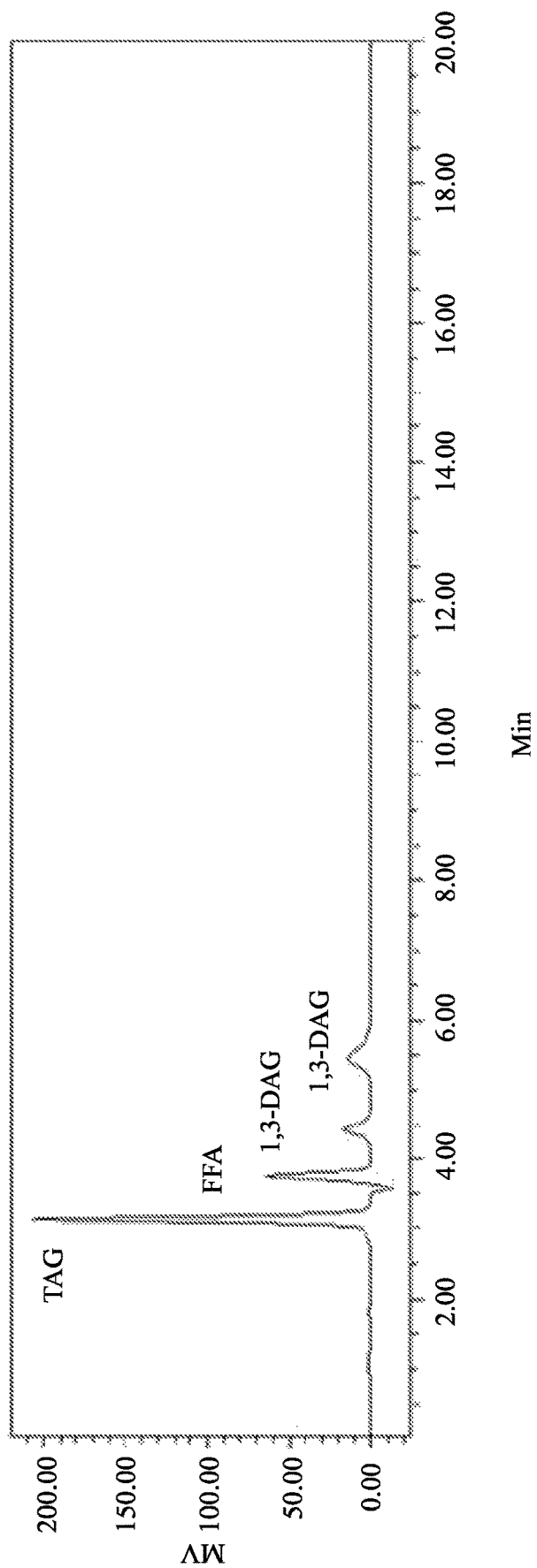

3.0 g of fish oil, 3 g of water and 960U (0.08%) of *Candida cylindracea* lipase were accurately weighed and added into the reactor with a magnetic stir bar and the reactor was sealed. The reactor was placed on a magnetic stirrer. The reactor was connected to a water circulation system and the water temperature was kept at 37° C. for 4 h. The hydrolysis rate is 16.9% (as shown in FIG. 2b). When the reaction completed, KOH-ethanol aqueous solution was used to remove free fatty acid after hydrolysis. After washing with water for three times, an upper, clear oil phase was collected and the solvent therein was evaporated to obtain the n-3 PUFAs-rich fish oil glyceride. In the fatty acid composition of glyceride products, the content of n-3 PUFAs is increased from 34.3% in the crude oil to 41.8% after hydrolysis.

Comparative Embodiment 2

Similar to Comparative Embodiment 1, except the type of aqueous solution in the reaction system of this embodiment was different, which was phosphate buffered solution (0.1 mol/L, pH 7), the rest of the procedures and conditions were identical. The hydrolysis rate and the content of n-3 PUFAs in glyceride obtained are shown in Table 1.

Comparative Embodiment 3

Similar to Comparative Embodiment 1, except the reaction time in the reaction system of this embodiment was different, which was 12 h, the rest of the procedures and conditions were identical. The hydrolysis rate and the content of n-3 PUFAs in glyceride obtained are shown in Table 1.

Comparative Embodiment 4

Similar to Embodiment 1, except the type of metal ion in the reaction system of this embodiment was different, which was sodium ion (0.1 mol/L), the rest of the procedures and conditions were identical. The hydrolysis rate and the content of n-3 PUFAs in glyceride obtained are shown in Table 1.

Comparative Embodiment 5

Similar to Embodiment 1, except the type of metal ion in the reaction system of this embodiment was different, which was potassium ion (0.1 mol/L), the rest of the procedures and conditions were identical. The hydrolysis rate and the content of n-3 PUFAs in glyceride obtained are shown in Table 1.

Comparative Embodiment 6

Similar to Comparative Embodiment 1, except the type of lipase in the reaction system of this embodiment was different, which was *Candida cylindracea* lipase, the rest of the procedures and conditions were identical. The hydrolysis rate and the content of n-3 PUFAs in glyceride obtained are shown in Table 1.

Comparative Embodiment 7

Similar to Comparative Embodiment 1, except the type of lipase in the reaction system of this embodiment was different, which was *Rhizopus oryzea* lipase, the rest of the procedures and conditions were identical. The hydrolysis rate and the content of n-3 PUFAs in glyceride obtained are shown in Table 1.

Comparative Embodiment 8

Similar to Comparative Embodiment 1, except the type of lipase in the reaction system of this embodiment was different, which was *Candida antarctica* lipase A, the rest of the procedures and conditions were identical. The hydrolysis rate and the content of n-3 PUFAs in glyceride obtained are shown in Table 1.

Comparative Embodiment 9

Similar to Comparative Embodiment 8, except the type of metal ion in the reaction system of this embodiment was different, which was sodium ion (0.1 mol/L), the rest of the procedures and conditions were identical. The hydrolysis rate and the content of n-3 PUFAs in glyceride obtained are shown in Table 1.

Comparative Embodiment 10

Similar to Comparative Embodiment 8, except the type of metal ion in the reaction system of this embodiment was different, which was potassium ion (0.1 mol/L), the rest of the procedures and conditions were identical. The hydrolysis rate and the content of n-3 PUFAs in glyceride obtained are shown in Table 1.

Comparative Embodiment 11

Similar to Comparative Embodiment 1, except the type of lipase in the reaction system of this embodiment was different, which was *Aspergillus* sp. lipase, the rest of the procedures and conditions were identical. The hydrolysis rate and the content of n-3 PUFAs in glyceride obtained are shown in Table 1.

Comparative Embodiment 12

Similar to Embodiment 1, except the type of lipase in the reaction system of this embodiment was different, which was monoacylglycerollipase, the rest of the procedures and conditions were identical. The hydrolysis rate and the content of n-3 PUFAs in glyceride obtained are shown in Table 1.

Comparative Embodiment 13

Similar to Comparative Embodiment 1, except the type of lipase in the reaction system of this embodiment was different, which was monoacylglycerollipase, the rest of the procedures and conditions were identical. The hydrolysis rate and the content of n-3 PUFAs in glyceride obtained are shown in Table 1.

Comparative Embodiment 14

Similar to Comparative Embodiment 13, but the reaction time of this embodiment was different, which was 12 h, the rest of the procedures and conditions were identical. The hydrolysis rate and the content of n-3 PUFAs in glyceride obtained are shown in Table 1.

Comparative Embodiment 15

Similar to Embodiment 1, except the type of lipase in the reaction system of this embodiment was different, which was immobilized lipase B from *Candida antarctica*, the rest of the procedures and conditions were identical. The hydrolysis rate and the content of n-3 PUFAs in glyceride obtained are shown in Table 1.

Comparative Embodiment 16

Similar to Comparative Embodiment 1, except the type of lipase in the reaction system of this embodiment was different, which was immobilized lipase B from *Candida antarctica*, the rest of the procedures and conditions were identical. The hydrolysis rate and the content of n-3 PUFAs in glyceride obtained are shown in Table 1.

Comparative Embodiment 17

Similar to Comparative Embodiment 16, but the reaction time of this embodiment was different, which was 12 h, the rest of the procedures and conditions were identical. The hydrolysis rate and the content of n-3 PUFAs in glyceride obtained are shown in Table 1.

See Table 1 for reaction conditions, hydrolysis rate and content of n-3 PUFAs in glyceride of Embodiments 1-42 and Comparative Embodiments 1-17.

TABLE 1

Reaction conditions, hydrolysis rate and content of n-3 PUFAs in glyceride of Embodiments 1-42 and Comparative Embodiments 1-17:

| | | Reaction conditions | | | | | | | Result | |
|---|---|---|---|---|---|---|---|---|---|---|
| Serial No. | Types of oils/metal ion liquid | Concentration of metal ions mmol/L | Types of lipases | Reaction time/h | Ph | Water-oil ratio m/m | Volume of addition of enzyme | Reaction temperature ° C. | Hydrolysis rate % | Content of n-3 PUFA in glyceride products (%) |
| Embodiment 1 | Fish oil/calcium ion—aqueous solution | 20 | *Candida cylindracea* lipase | 2 | — | 1:1 | 960 U | 37 | 41.2 | 60.3 |

TABLE 1-continued

Reaction conditions, hydrolysis rate and content of n-3 PUFAs in glyceride of Embodiments 1-42 and Comparative Embodiments 1-17:

| Serial No. | Types of oils/metal ion liquid | Concentration of metal ions mmol/L | Types of lipases | Reaction time/h | Ph | Water-oil ratio m/m | Volume of addition of enzyme | Reaction temperature ° C. | Hydrolysis rate % | Content of n-3 PUFA in glyceride products (%) |
|---|---|---|---|---|---|---|---|---|---|---|
| Embodiment 2 | Fish oil/magnesium ion—aqueous solution | 20 | *Candida cylindracea* lipase | 2 | — | 1:1 | 960 U | 37 | 36.1 | 55.9 |
| Embodiment 3 | Fish oil/manganese ion—aqueous solution | 20 | *Candida cylindracea* lipase | 2 | — | 1:1 | 960 U | 37 | 33.5 | 52.4 |
| Embodiment 4 | Fish oil/ferric ion—aqueous solution | 20 | *Candida cylindracea* lipase | 2 | — | 1:1 | 960 U | 37 | 27.9 | 50.1 |
| Embodiment 5 | Fish oil/calcium ion—phosphate buffered solution | 20 | *Candida cylindracea* lipase | 2 | 7 | 1:1 | 960 U | 37 | 43.5 | 62.1 |
| Embodiment 6 | Fish oil/calcium ion—citrate buffered solution | 20 | *Candida cylindracea* lipase | 2 | 7 | 1:1 | 960 U | 37 | 42.3 | 62.0 |
| Embodiment 7 | Fish oil/magnesium ion—phosphate buffered solution | 20 | *Candida cylindracea* lipase | 2 | 7 | 1:1 | 960 U | 37 | 36.2 | 56.3 |
| Embodiment 8 | Fish oil/calcium ion—aqueous solution | 10 | *Candida cylindracea* lipase | 2 | — | 1:1 | 960 U | 37 | 32.4 | 53.6 |
| Embodiment 9 | Fish oil/calcium ion—aqueous solution | 40 | *Candida cylindracea* lipase | 2 | — | 1:1 | 960 U | 37 | 41.9 | 60.7 |
| Embodiment 10 | Fish oil/calcium ion—aqueous solution | 20 | *Candida cylindracea* lipase | 2 | — | 1:1 | 960 U | 37 | 41.0 | 59.3 |
| Embodiment 11 | Fish oil/magnesium ion—aqueous solution | 20 | *Candida cylindracea* lipase | 2 | — | 1:1 | 960 U | 37 | 35.3 | 55.2 |
| Embodiment 12 | Fish oil/manganese ion—aqueous solution | 20 | *Candida cylindracea* lipase | 2 | — | 1:1 | 960 U | 37 | 26.5 | 49.1 |
| Embodiment 13 | Fish oil/ferric ion—aqueous solution | 20 | *Candida cylindracea* lipase | 2 | — | 1:1 | 960 U | 37 | 21.0 | 44.0 |
| Embodiment 14 | Fish oil/calcium ion—aqueous solution | 20 | *Rhizopus oryzea* lipase | 2 | — | 1:1 | 960 U | 37 | 30.6 | 50.9 |

TABLE 1-continued

Reaction conditions, hydrolysis rate and content of n-3 PUFAs in glyceride
of Embodiments 1-42 and Comparative Embodiments 1-17:

| Serial No. | Types of oils/metal ion liquid | Concentration of metal ions mmol/L | Types of lipases | Reaction time/h | Ph | Water-oil ratio m/m | Volume of addition of enzyme | Reaction temperature °C. | Hydrolysis rate % | Content of n-3 PUFA in glyceride products (%) |
|---|---|---|---|---|---|---|---|---|---|---|
| Embodiment 15 | Fish oil/magnesium ion—aqueous solution | 20 | *Rhizopus oryzea* lipase | 2 | — | 1:1 | 960 U | 37 | 26.8 | 48.3 |
| Embodiment 16 | Fish oil/manganese ion—aqueous solution | 20 | *Rhizopus oryzea* lipase | 2 | — | 1:1 | 960 U | 37 | 20.9 | 42.3 |
| Embodiment 17 | Fish oil/ferric ion—aqueous solution | 20 | *Rhizopus oryzea* lipase | 2 | — | 1:1 | 960 U | 37 | 21.6 | 44.7 |
| Embodiment 18 | Fish oil/calcium ion—aqueous solution | 20 | *Candida antarctica* lipase A | 2 | — | 1:1 | 960 U | 37 | 33.9 | 52.3 |
| Embodiment 19 | Fish oil/magnesium ion—aqueous solution | 20 | *Candida antarctica* lipase A | 2 | — | 1:1 | 960 U | 37 | 34.6 | 52.9 |
| Embodiment 20 | Fish oil/manganese ion—aqueous solution | 20 | *Candida antarctica* lipase A | 2 | — | 1:1 | 960 U | 37 | 30.8 | 47.6 |
| Embodiment 21 | Fish oil/ferric ion—aqueous solution | 20 | *Candida antarctica* lipase A | 2 | — | 1:1 | 960 U | 37 | 23.6 | 44.0 |
| Embodiment 22 | Fish oil/calcium ion—aqueous solution | 20 | *Aspergillus sp.* lipase | 2 | — | 1:1 | 960 U | 37 | 30.9 | 50.3 |
| Embodiment 23 | Fish oil/magnesium ion—aqueous solution | 20 | *Aspergillus sp.* lipase | 2 | — | 1:1 | 960 U | 37 | 26.3 | 46.3 |
| Embodiment 24 | Fish oil/manganese ion—aqueous solution | 20 | *Aspergillus sp.* lipase | 2 | — | 1:1 | 960 U | 37 | 35.6 | 51.7 |
| Embodiment 25 | Fish oil/ferric ion—aqueous solution | 20 | *Aspergillus sp.* lipase | 2 | — | 1:1 | 960 U | 37 | 28.3 | 46.1 |
| Embodiment 26 | Algal oil/calcium ion—aqueous solution | 20 | *Candida cylindracea* lipase | 2 | — | 1:1 | 960 U | 37 | 39.4 | 68.7 |
| Embodiment 27 | Algal oil/magnesium ion—aqueous solution | 20 | *Candida cylindracea* lipase | 2 | — | 1:1 | 960 U | 37 | 32.6 | 61.3 |

TABLE 1-continued

Reaction conditions, hydrolysis rate and content of n-3 PUFAs in glyceride of Embodiments 1-42 and Comparative Embodiments 1-17:

| Serial No. | Types of oils/metal ion liquid | Concentration of metal ions mmol/L | Types of lipases | Reaction time/h | Ph | Water-oil ratio m/m | Volume of addition of enzyme | Reaction temperature °C. | Hydrolysis rate % | Content of n-3 PUFA in glyceride products (%) |
|---|---|---|---|---|---|---|---|---|---|---|
| Embodiment 28 | Algal oil/calcium ion—phosphate buffered solution | 20 | Candida cylindracea lipase | 2 | 7 | 1:1 | 960 U | 37 | 39.3 | 68.8 |
| Embodiment 29 | Algal oil/calcium ion—phosphate buffered solution | 20 | Candida cylindracea lipase | 2 | 7 | 1:1 | 960 U | 37 | 39.3 | 68.8 |
| Embodiment 30 | Algal oil/calcium ion—phosphate buffered solution | 20 | Rhizopus oryzea lipase | 2 | 7 | 1:1 | 960 U | 37 | 39.3 | 68.8 |
| Embodiment 31 | Algal oil/calcium ion—phosphate buffered solution | 20 | Candida antarctica lipase A | 2 | 7 | 1:1 | 960 U | 37 | 39.3 | 68.8 |
| Embodiment 32 | Algal oil/calcium ion—phosphate buffered solution | 20 | Aspergillus sp. lipase | 2 | 7 | 1:1 | 960 U | 37 | 39.3 | 68.8 |
| Embodiment 33 | Fish oil/calcium ion—aqueous solution | 20 | Candida cylindracea lipase | 1 | — | 1:1 | 960 U | 37 | 31.5 | 52.3 |
| Embodiment 34 | Fish oil/calcium ion—aqueous solution | 20 | Candida cylindracea lipase | 4 | — | 1:1 | 960 U | 37 | 44.3 | 63.1 |
| Embodiment 35 | Fish oil/calcium ion—phosphate buffered solution | 20 | Candida cylindracea lipase | 2 | 5 | 1:1 | 960 U | 37 | 30.3 | 50.3 |
| Embodiment 36 | Fish oil/calcium ion—phosphate buffered solution | 20 | Candida cylindracea lipase | 2 | 8 | 1:1 | 960 U | 37 | 28.6 | 48.9 |
| Embodiment 37 | Fish oil/calcium ion—aqueous solution | 20 | Candida cylindracea lipase | 2 | — | 0.3:1 | 960 U | 37 | 33.1 | 54.0 |
| Embodiment 38 | Fish oil/calcium ion—aqueous solution | 20 | Candida cylindracea lipase | 2 | — | 2:1 | 960 U | 37 | 40.6 | 59.3 |
| Embodiment 39 | Fish oil/calcium ion—aqueous solution | 20 | Candida cylindracea lipase | 2 | — | 1:1 | 240 U | 37 | 26.3 | 47.7 |
| Embodiment 40 | Fish oil/calcium ion— | 20 | Candida cylindracea lipase | 2 | — | 1:1 | 9600 U | 37 | 43.6 | 62.8 |

TABLE 1-continued

Reaction conditions, hydrolysis rate and content of n-3 PUFAs in glyceride of Embodiments 1-42 and Comparative Embodiments 1-17:

| Serial No. | Types of oils/metal ion liquid | Concentration of metal ions mmol/L | Types of lipases | Reaction time/h | Ph | Water-oil ratio m/m | Volume of addition of enzyme | Reaction temperature °C. | Hydrolysis rate % | Content of n-3 PUFA in glyceride products (%) |
|---|---|---|---|---|---|---|---|---|---|---|
| Embodiment 41 | Fish oil/calcium ion—aqueous solution | 20 | *Candida cylindracea* lipase | 2 | — | 1:1 | 960 U | 20 | 29.9 | 48.3 |
| Embodiment 42 | Fish oil/calcium ion—aqueous solution | 20 | *Candida cylindracea* lipase | 2 | — | 1:1 | 960 U | 50 | 30.6 | 48.1 |
| Comparative Embodiment 1 | Fish oil/water | 20 | *Candida cylindracea* lipase | 4 | — | 1:1 | 960 U | 37 | 16.9 | 41.8 |
| Comparative Embodiment 2 | Fish oil/phosphate buffered solution | 20 | *Candida cylindracea* lipase | 4 | 7 | 1:1 | 960 U | 37 | 19.0 | 42.5 |
| Comparative Embodiment 3 | Fish oil/water | 20 | *Candida cylindracea* lipase | 12 | — | 1:1 | 960 U | 37 | 38.6 | 58.9 |
| Comparative Embodiment 4 | Fish oil/sodium ion—aqueous solution | 20 | *Candida cylindracea* lipase | 4 | — | 1:1 | 960 U | 37 | 17.3 | 41.7 |
| Comparative Embodiment 5 | Fish oil/potassium ion—aqueous solution | 20 | *Candida cylindracea* lipase | 4 | — | 1:1 | 960 U | 37 | 18.0 | 42.0 |
| Comparative Embodiment 6 | Fish oil/water | 20 | *Candida cylindracea* lipase | 4 | — | 1:1 | 960 U | 37 | 14.6 | 40.9 |
| Comparative Embodiment 7 | Fish oil/water | 20 | *Rhizopus oryzea* lipase | 4 | — | 1:1 | 960 U | 37 | 14.9 | 39.8 |
| Comparative Embodiment 8 | Fish oil/water | 20 | *Candida antarctica* lipase A | 4 | — | 1:1 | 960 U | 37 | 15.6 | 40.9 |
| Comparative Embodiment 9 | Fish oil/sodium ion—aqueous solution | 20 | *Candida antarctica* lipase A | 4 | — | 1:1 | 960 U | 37 | 16.0 | 40.0 |
| Comparative Embodiment 10 | Fish oil/potassium ion—aqueous solution | 20 | *Candida antarctica* lipase A | 4 | — | 1:1 | 960 U | 37 | 15.1 | 39.3 |
| Comparative Embodiment 11 | Fish oil/water | 20 | *Aspergillus sp.* lipase | 4 | — | 1:1 | 960 U | 37 | 13.6 | 39.8 |
| Comparative Embodiment 12 | Fish oil/calcium ion—aqueous solution | 20 | monoacylglycerollipase | 4 | — | 1:1 | 960 U | 37 | 13.4 | 40.3 |
| Comparative Embodiment 13 | Fish oil/water | 20 | monoacylglycerollipase | 4 | — | 1:1 | 960 U | 37 | 12.6 | 39.8 |

TABLE 1-continued

Reaction conditions, hydrolysis rate and content of n-3 PUFAs in glyceride of Embodiments 1-42 and Comparative Embodiments 1-17:

| | | Reaction conditions | | | | | | | Result | |
|---|---|---|---|---|---|---|---|---|---|---|
| Serial No. | Types of oils/metal ion liquid | Concentration of metal ions mmol/L | Types of lipases | Reaction time/h | Ph | Water-oil ratio m/m | Volume of addition of enzyme | Reaction temperature ° C. | Hydrolysis rate % | Content of n-3 PUFA in glyceride products (%) |
| Comparative Embodiment 14 | Fish oil/water | 20 | monoacylglycerollipase | 12 | — | 1:1 | 960 U | 37 | 25.3 | 45.6 |
| Comparative Embodiment 15 | Fish oil/calcium ion—aqueous solution | 20 | immobilized lipase B from Candida antarctica | 4 | — | 1:1 | 960 U | 37 | 17.9 | 41.0 |
| Comparative Embodiment 16 | Fish oil/water | 20 | immobilized lipase B from Candida antarctica | 4 | — | 1:1 | 960 U | 37 | 17.6 | 40.2 |
| Comparative Embodiment 17 | Fish oil/water | 20 | immobilized lipase B from Candida antarctica | 12 | — | 1:1 | 960 U | 37 | 27.6 | 44.6 |

In the above table(s), "—" represents that the aqueous solution is selected from water.

By comparing the results of Embodiments 1-9 with those of Comparative Embodiments 1-3 in Table 1, the hydrolysis rate of fish oil obtained by the methods using 2 h of reaction time is greatly improved, which is as high as over 40%. In addition, the content of n-3 PUFAs in glyceride is as high as over 60%, which is much better than that obtained from the reaction system after 4 h of reaction without metal ions (such as Comparative Embodiments 1 and 2), and even some performances of those embodiments are comparable to or even better than those after 12 h of reaction according to the method of Comparative Embodiment 3. It can be seen that when lipase is Candida cylindracea lipase, the presence of metal ions $Ca^{2+}$, $Mg^{2+}$, $Mn^{2+}$ and $Fe^{3+}$ significantly improves the hydrolysis rate of lipase and shortens the reaction time. Meanwhile, by comparing between the following pairs: Embodiments 10-13 and Comparative Embodiment 6; Embodiments 14-17 and Comparative Embodiment 7; Embodiments 18-21 and Comparative Embodiment 8; Embodiments 22-25 and Comparative Embodiment 11, when lipase is Candida cylindracea lipase, Rhizopus oryzae lipase, Candida antarctica lipase A or Aspergillus sp. lipase, the presence of metal ions $Ca^{2+}$, $Mg^{2+}$, $Mn^{2+}$ and $Fe^{3+}$ significantly improves the hydrolysis rate of lipase and shortens the reaction time. In addition, the promotion effect of metal ions of $Ca^{2+}$ and $Mg^{2+}$ is much better.

From the results of Embodiments 26-32, the presence of metal ions $Ca^{2+}$, $Mg^{2+}$, $Mn^{2+}$ and $Fe^{3+}$ is also able to improve the hydrolysis efficiency of lipase in algae oil. Apparently, the method of this invention is also applicable to other oils containing n-3 polyunsaturated fatty acids.

From the results of Embodiments 5, 33 and 34, the method of this invention is also able to greatly improve enzymatic hydrolysis efficiency when the reaction time is 1 h and the hydrolysis degree increases with an increase in reaction time, but the increase is not very significant.

From the results of Embodiment 1 and Comparative Embodiments 1, 4-5, as well as Embodiment 18 and Comparative Embodiments 8-10, when metal ions are selected from potassium ions or sodium ions, the hydrolysis efficiency of lipase in this invention is not improved, demonstrating that only specific metal ions used in the present invention have the effect on improving the hydrolysis efficiency of lipase.

From the results of Comparative Embodiments 13-17, when calcium ions are added into the system where the lipase is selected from monoacylglycerollipase or immobilized lipase B from Candida antarctica, there is no improvement on enzymatic hydrolysis efficiency of lipase. Therefore, only metal ions used in the present invention have promotion effect on the specific enzyme. It means that, only specific metal ions and corresponding specific lipases are able to shorten the hydrolysis process of oils.

Though this invention has been disclosed as above through the relatively superior embodiments, those embodiments are not used to limit this invention. Anyone who knows this technology is permitted to make various changes and modifications without departing from the spirit and scope of this invention. Therefore, the protection scope of this invention shall be subject to that defined by the claims.

What is claimed is:

1. A method for improving eicosapentaenoic acid (EPA) and/or docosahexaenoic acid (DHA) glyceride enrichment efficiency, the method comprising:
   providing an oil, a lipase, metal ions and an aqueous solution in a reaction system, wherein the oil comprises EPA and/or DHA;
   obtaining a mixture of the oil, lipase, metal ions and aqueous solution after a reaction time in the reaction system at pH 5-8 and at 20-50° C.; and
   removing free fatty acid from the mixture to obtain a EPA and/or DHA-rich glyceride,
   wherein the lipase is selected from Candida cylindracea lipase, Rhizopus oryzae lipase, Candida antarctica lipase A of Candida antarctica, or one or more of Aspergillus sp. lipase,
   wherein the metal ions comprising one or more of calcium ions, magnesium ions, manganese ions (2+) and ferric ions (3+), and wherein the aqueous solution comprises one or more of pure water solution, phosphate buffered solution and citrate buffered solution.

2. The method according to claim 1, wherein concentration of the metal ions is 5-50 mmol/L.

3. The method according to claim 1, wherein concentration of the buffer salt solution is 0.05-0.5 mol/L.

4. The method according to any one of claim 1, wherein mass ratio of the aqueous solution to the oil is 0.2-3:1.

5. The method according to any one of claim 1, wherein the reaction time is 1-12 h.

6. The method according to any one of claim 1, wherein volume of the lipase added into the reaction system is 150-15000U/g oil.

7. The method according to claim 5, wherein the reaction time is 1-4 h.

8. The method according to claim 1, wherein the oil is selected from an animal oil, a microbial oil or a plant oil.

* * * * *